United States Patent [19]

Watson et al.

[11] Patent Number: 4,665,026

[45] Date of Patent: May 12, 1987

[54] ENZYMATIC SYNTHESIS OF (S)3-HYDROXY-3-METHYLGLUTARYL COENZYME A

[76] Inventors: John A. Watson, 78 Santa Ana, Daly City, Calif. 94015; Christopher M. Havel, 315 3rd St., Montera, Calif. 94037

[21] Appl. No.: 617,410

[22] Filed: Jun. 4, 1984

[51] Int. Cl.$^4$ .................. C12N 9/18; C12P 11/00; C12R 1/38

[52] U.S. Cl. .................. 435/130; 435/195; 435/874

[58] Field of Search .................. 435/89, 90, 91, 92, 435/130, 197, 874

[56] References Cited

PUBLICATIONS

Rilling et al.; "The Enzymatic Isomerization of β-Methylvinylacetyl Coenzyme A and the Specificity of a Bacterial β-Methylcrotonyl Coenzyme A Carboxylase"; *J. Biol. Chem.*, vol. 235, No. 11, 1960, pp. 3087–3092.

Coon, M. J.; "Enzymes of Isovaleryl CoA Metabolism"; *Methods in Enzymology*, vol. V; 1962; pp. 896–899.

Lehninger, "Biochemistry", Worth Publishing Co., 1970, p. 443.

U. Henning, (1959), Archives of Biochemistry and Biophysics, 83:259–267.

R. Ray Fall, (1981), Methods in Enzymology 71:791–799.

*Primary Examiner*—Thomas G. Wiseman
*Assistant Examiner*—Elizabeth C. Weimar

[57] ABSTRACT

A novel method for the production of (S)3-hydroxy-3-methylglutaryl coenzyme A provided for the enzymatic conversion of 3-methylcrotonyl coenzyme A to the desired product. The enzyme is obtained from *Pseudomonas citronellolis* by ammonium sulfate precipitation of a cellular lysate. The precipitate is then redissolved in a suitable buffer and yields of over 60% have been obtained by direct reaction in the buffer.

3 Claims, No Drawings

ENZYMATIC SYNTHESIS OF (S)3-HYDROXY-3-METHYLGLUTARYL COENZYME A

BACKGROUND OF THE INVENTION

1. Field Of The Invention (S)3-Hydroxy-3-methylglutaryl coenzyme A ((S)HMG-CoA) is a substrate in many known biological reactions, including the production of 3-methyl glutaconyl coenzyme A, acetyl coenzyme A, and mevalonate. The last reaction is the most studied and is catalyzed by the enzyme HMG-CoA reductase (EC 1.1.1.34). Mevalonate is the unique precursor for the synthesis of isoprenoids, including sterols, sex hormones, pheromones, carotenoids, rubber, and the like. The availability of large amounts of biologically active (S)HMG-CoA is desirable for the study of these biologically important reactions.

Heretofore, commercial sources for HMG-CoA have relied on a chemical synthesis utilizing 3-hydroxy-3-methylglutaryl anhydride and coenzyme A which yields a racemic mixture of the biologically-active (S) isomer and the biologically-inactive (R) isomer. Such mixtures, at best, yield only one-half the biological activity of pure (S)HMG-CoA. Moreover, it has been found by the inventors herein that the (R) isomer is a competitive inhibitor of the (S) isomer in the conversion of the (S) isomer to mevalonate. Thus, it would be highly desirable to provide an efficient, economic synthesis for (S)HMG-CoA which results in a product free of the (R) isomer.

2. Description of the Prior Art

Henning, et al. (1959) *Arch. Biochem. Biophys.*, 83:259, describe a two-step synthesis of (S)HMG-CoA which uses partially purified enzymes from sheep liver and bacteria.

SUMMARY OF THE INVENTION

A novel method for the enzymatic synthesis of (S)HMG-CoA utilizes an enzyme fraction obtained by ammonium sulfate precipitation of a cellular lysate of *Pseudomonas citronellolis*. The reaction protocol provides for the enzymatic conversion of 3-methylcrotonyl coenzyme A to (S)HMG-CoA in the presence of a carbon dioxide source, adenosine triphosphate, and a divalent metal cation, e.g., $Mg^{+2}$ or $Mn^{+2}$. Conveniently, the carbon source may be radiolabeled to provide for a radiolabeled product. The reaction protocol of the present invention is particularly convenient in that it can be carried out in a single reaction step, provides for enhanced substrate activity, and eliminates the waste of radioactive label inherent in prior art methods where radiolabeled (R) isomer is produced.

DESCRIPTION OF THE SPECIFIC EMBODIMENTS

The method of the present invention relies on the following reaction for the synthesis of (S)HMG-CoA.

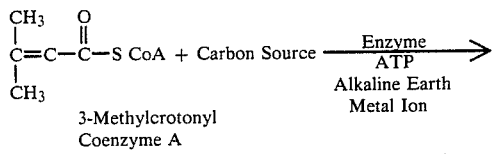

3-Methylcrotonyl Coenzyme A

-continued $$\underset{\text{(S)HMG—CoA}}{\text{CH}_3-\underset{\underset{*\text{CO}_2}{|}}{\overset{\overset{\text{OH}}{|}}{\text{C}}}-\text{CH}_2-\overset{\overset{\text{O}}{\|}}{\text{C}}-\text{S CoA}} \underset{}{\overset{\text{H}_2\text{O}}{\rightleftarrows}} \underset{\beta\text{-Methylglutaconyl Coenzyme A}}{\overset{\overset{\text{CH}_3}{|}}{\underset{\underset{*\text{CO}_2}{|}}{\text{C}}}=\text{CH}-\overset{\overset{\text{O}}{\|}}{\text{C}}-\text{S CoA}}$$

The conversion of 3-methylcrotonyl coenzyme A to (S)HMG-CoA is catalyzed by 3-methylcrotonyl coenzyme A carboxylase. In the present invention, the enzyme is obtained from *Pseudomonas citronellolis* (ATCC 13674 available on an unrestricted basis) by precipitation with ammonium sulfate. The bacteria can be grown in any suitable nutrient medium containing from about 0.1 to 0.5 weight percent isovaleric acid or leucine to induce the synthesis of 3-methylcrotonyl coenzyme A carboxylase. After growing the bacteria to a suitable density, e.g., an optical density of at least about 1, the bacteria may be lysed by the method described in *Methods In Enzymology*, 71:791 (1981). Briefly, the cells are harvested, washed, and disrupted with a French press. The resulting cellular lysate is then precipitated with ammonium sulfate to provide an enzyme composition having sufficient enzyme to give 70% product of coenzyme esters (acid stable carboxy) when the composition is combined with the appropriate substrates and cofactors. Usually, this will be up to about 40% ammonium sulfate saturation. Further purification may be achieved by reprecipitation at about 35-39% ammonium sulfate. The ammonium sulfate precipitate is dissolved in a suitable buffer, e.g., HEPES buffer, to a protein concentration in the range from about 20 to 40 mg/ml and used for the synthesis of (S)HMG-CoA.

Suitable carbon dioxide sources include carbonate salts, such as sodium carbonate, sodium bicarbonate, and the like, which yield the carbonate ion in aqueous solution. By providing a radiolabeled carbonate salt, the (S)HMG-CoA product (as well as mevalonate and other products of (S)HMG-CoA) may be radiolabeled. For example, use of labeled sodium bicarbonate ($NaH[^{14}CO_3]$) results in labeled carbons where indicated by the asterisk (*) in the formula above. Another suitable carbon source is $\beta,\beta$-dimethylacrylic acid, which can be synthesized from $^{14}CO_2$ and 1-chloro-3-methylpropene (Yuan and Bloch (1959) J. Biol. Chem. 234:2605) to yield $\beta,\beta$-dimethylacrylic acid-$[1-^{14}C]$, which in turn provides $[1-^{14}C]$-3-hydroxy-3-methylglutaryl coenzyme A and $[5-^{14}C]$-mevalonate when utilized in the present invention. Alternatively, the (S)HMG-CoA and other products may be labelled by utilizing appropriately labelled 3-methylcrotonyl coenzyme A as a reactant.

The above reaction proceeds in the presence of ATP at a concentration from about 3 to 10mM, usually about 5mM, and a divalent metal cation (usually $Mg^{+2}$ or $Mn^{+2}$) at a concentration of about 2 to 5mM.

The reactants are mixed in the buffer containing the enzyme precipitate, at a temperature in the range of about 10 to 70° C., usually at about 37° C. After approximately 10 to 25 minutes, reaction is terminated. When preparing radiolabelled product, the reaction is terminated after the amount of fixed label has reached a plateau. The terminated reaction mixture may be purified by preparative high-performance liquid chromatography, and the isolated peak lyophilized and stored in 1mM HCl until use.

While the above provides a full and complete disclosure of the preferred embodiments of the invention, various modifications, alternate constructions, and equivalents may be employed without departing from the true spirit and scope of the invention. Therefore, the above description and illustrations should not be construed as limiting the scope of the invention which is defined by the appended claims.

What is claimed is:

1. A method for preparing (S)3-hydroxy-3-methylglutaryl coenzyme A, which comprises:

combining in a buffured medium, 3-methylcrotonyl coenzyme A, a carbon dioxide source, ATP at a concentration in the range of about 3 to 10 mM, a divalent metal cation at a concentration in the range of about 2 to 5 mM, from about 20 to 40 mg/ml of partially purified 3-methylcrotonyl coenzyme A carboxylase capable of seventy percent conversion of substrate to product;

incubating said medium for a sufficient time for the concentration of (S)3-hydroxy-3-methylglutaryl coenzyme A to substantially reach a product plateau; and purifying said (S)3-hydroxy-3-methylglutosyl coenzyme A, wherein said partially purified carboxylase is directly produced by precipitating it from a 40% saturation concentration of ammonium sulfate or by precipitating it from a *Pseudomonas citronellis* lysate with a 40% saturation concentration of ammonium sulfate followed by redispersing said precipitate in a buffered medium and reprecipitating at a concentration of about 35 to 39% ammonium sulfate saturation.

2. A method according to claim 1, wherein said metal cation is manganese or magnesium.

3. A method according to claim 1, wherein said carbon dioxide source is radioactive bicarbonate.

* * * * *